United States Patent [19]

Oppenheimer et al.

[11] Patent Number: 4,980,169

[45] Date of Patent: Dec. 25, 1990

[54] FLAVOR ENHANCING AND INCREASING EFFICACY OF COUGH DROPS

[75] Inventors: Alfred Oppenheimer, Randolph; Ralph Cifrese, Wharton; Mamoun M. Hussein, Mt. Lakes; Vincent Corsello, Cedar Knolls, all of N.J.

[73] Assignee: Warner-Lambert Company, Morris Plains, N.J.

[21] Appl. No.: 518,360

[22] Filed: May 3, 1990

[51] Int. Cl.$^5$ .............................................. A61K 9/20
[52] U.S. Cl. .................................. 424/439; 424/195.1; 424/440; 424/441; 424/465; 514/974
[58] Field of Search ............ 424/440, 441, 439, 195.1, 424/465; 514/974

[56] References Cited

U.S. PATENT DOCUMENTS

| | | | |
|---|---|---|---|
| 3,998,974 | 12/1976 | Zaffaroni | 426/534 |
| 4,404,184 | 9/1983 | Pittet | 424/49 |
| 4,454,111 | 6/1984 | Boden | 424/58 |

Primary Examiner—Thurman K. Page
Assistant Examiner—D. Gabrielle Phelan
Attorney, Agent, or Firm—Daniel A. Scola, Jr.

[57] ABSTRACT

A novel confection containing a volatile oil for dissolving in the oral cavity is disclosed. The confection contains a sensorially undetectable amount of a volatile oil modifying agent which enhances the flavor of the volatile oil as well as ameliorates the perception of unpleasant organoleptic sensations such as bitterness initiated by the volatile oil being released in the oral cavity. In a preferred embodiment, the modifying agent is capsicum and most preferably, the oleoresin form of capsicum.

10 Claims, No Drawings

FLAVOR ENHANCING AND INCREASING EFFICACY OF COUGH DROPS

BACKGROUND OF THE INVENTION

The present invention relates to improved formulations for confections which are intended to reside in the oral cavity for a period of time while being consumed. In particular, the present invention provides, among other things, medicinal tablets with enhanced flavored delivery as the confection dissolves in the oral cavity.

Confections, especially medicinal tablets which deliver active ingredients in the oral cavity, are well known in the art and may be divided into various classes based upon their composition or intended effect. Examples include lozenges, compressed tablets and other medicinal tablets. The confections may have breath fresheners, breath deodorants, cough suppressants, nasal decongestants and the like.

Over the years, considerable effort has been directed to improving sensory perception in the oral cavity of the volatile oils contained in confections. Volatile oils or essential oils are derived from the leaves, stems or flowers of numerous plants and usually carry the savory or odorous principles of the plant which is obtained by distillation, expression or extraction. Volatile oils are known for their variable odors and distinctive tastes. The odors of volatile oils are modified by exposure to air, and the tastes of the volatile oils are quite distinctive. Some are sweet, while others can be mild, pungent, hot, acrid, caustic or burning in taste. In addition, some volatile oils can be made synthetically.

Enhancing the impact of the volatile oils in the oral cavity increases the benefit of the confection by ameliorating perceived bitterness, pungency, or other undesirable organoleptic sensations.

Menthol is isolated principally from the oil of *Mentha arvensis*. In its commercial form, menthol is present as crystals obtained from a process involving cooling of the above mentioned oil. Fractional distillation of peppermint oil which usually contains from about 50% to about 65% menthol provides another important source of menthol. In addition, menthol can be provided synthetically.

The use of menthol, for example, for its medicinal effect is known in the art. Menthol's cooling effect to the mouth is useful to relieve local irritations in the throat and mouth.

Eucalyptus is another essential oil often combined with other essential oils such as menthol in confection formulations to impart medicinal effect. In particular, eucalyptus is believed to exhibit an expectorant action. The combination of the essential oils of menthol and eucalyptus, in a formulation capable of dissolving in the oral cavity provide a useful medicinal preparation in treatment of coughs and minor mouth, throat, and upper respiratory irritations.

Confections which include such medicinal formulations, e.g., cough drops, lozenges, etc., however, suffer from several shortcomings. For example, bitterness is often perceived due to the high potency of the essential oils which contain menthol. The bitterness of the menthol released in the oral cavity, therefore, provides an unpleasant organoleptic experience to the user thus reducing the likelihood of continued treatment with the lozenge or tablet. In addition, prior art preparations containing menthol suffer from reduced efficacy due to the erratic release of the menthol contained within the confection. Consequently, the cooling effect of menthol has often been attenuated. These problems, therefore, tend to detract from the acceptance of menthol-containing products as adjuncts in cough and cold therapy.

Other confectionery products, which may contain menthol or other flavorants derived from essential oils, such as spearmint, and/or peppermint, have also been known to produce bitterness while residing in the oral cavity.

While not an essential oil, the fruits of various species of capsicum are often added to food preparations to impart a pungent taste. Capsicum generally refers to various types of pepper of varying degrees of pungency. Capsicum oleoresin is an extract of fruits from various capsicum species and consists of a resinous matter and a liquid phase. The capsicum oleoresin is extremely pungent. For example, a dilution of one part of capsicum oleoresin in five million parts of 9% sugar water at 10° C. produces a distinct burning effect in the throat and posterior region of the oral cavity. The capsicum oleoresin, with its characteristic peppery odor and extremely high bite, provides a useful source of aromas and is useful as an additive in various condiments, sauces and other foods. The traditional use of capsicum, therefore, is to provide a peppery heat sensation or spicy bite to foods or other confectionery items.

In the past, capsicum has generally been limited to those uses which rely on its peppery hot sensation or bite properties. U.S. Pat. No. 4,198,393 to Yoshida et al., discloses using cyclic acetals of 2-methyl-2-pentenal with capsicum and volatile oils, to provide flavor compounds that demonstrate a primary flavor taste and a purported etherial effect.

U.S. Pat. No. 4,420,472 to Boden, et al. discloses the use of prenyl methyl carbonate to enhance the flavor and aroma of chewing gums, toothpaste and medicinal products containing various flavor adjuvants including capsicum and other black pepper oleoresins as well as numerous volatile oils.

U.S. Pat. No. 4,197,328 to Sprecker, et al. discloses the use of oxabicyclooctanes to augment or enhance a variety of flavors and fragrances in various consumable materials. Similar to Yoshida, et al., capsicum and various volatile oils are among possible co-ingredients used as a flavor adjuvants enhanced by the oxabicyclooctanes.

U.S. Pat. No. 4,423,030 to Hayes, et al. discloses dental creams or mouthwashes having "two-tone flavors" provided by an essential oil component comprising about 0.01–5% by weight and a water-insoluble oleoresin component comprising about 0.001–0.1% by weight. Capsicum varieties are included among the oleoresins and are relied upon to provide a sensation of pungency different from that provided by the essential oil.

It is, therefore, an object of the present invention to provide an improved confection having essential oils with reduced perception of bitterness upon the release of the essential oil into the oral cavity.

Another object of the present invention is to provide a natural food additive which enhances the flavor and organoleptic sensation o essential oils in the oral cavity.

SUMMARY OF THE INVENTION

In accordance with the present invention, there is provided an improved confection composition containing a volatile oil which enhances the organoleptic perception of the volatile oil as the confection dissolves in the oral cavity. The new composition includes a volatile oil-modifying agent which ameliorates perceived undesirable organoleptic sensations such as bitterness. The volatile oil-modifying agent is present in an amount which is sensorially undetected in the oral cavity so that the desired aroma and flavor of the volatile oil is perceived without detecting the modifying agent.

In a preferred embodiment, the volatile oil modifying agent is capsicum. In a most preferred embodiment the capsicum is present in the oleoresin form. The modifying agent may be present in an amount of from about 1 to about 150 parts per million (ppm) of the confection by weight, preferably in an amount of from about 5 to about 80 ppm, and most preferably from about to about 9 to about 50 ppm.

The flavor and aroma imparting properties of the confection can be provided by volatile oils selected from both natural and synthetic sources. Typically, the volatile oil is present in an amount of from about 0.05 to about 1.0% by weight of the confection. The amount of volatile oil varies, however, in accordance with the desired flavor and aroma of the confection product. In addition, the confection may contain a blend of volatile oils and other sweeteners to provide the desired flavor in the oral cavity. Examples of suitable volatile oils include spearmint, eucalyptus, peppermint, menthol and wintergreen (methyl salicylate) oils. Additionally, the confections of the present invention can also include sweeteners such as sugar, sugar alcohols, and artificial sweeteners.

In one embodiment, there is provided a confection containing a blend of eucalyptus and 1-menthol and the modifying agent to ameliorate the perceived bitterness of the volatile oil combination. The above-mentioned combination is useful in cough and cold therapy as well as having a decongestant effect in the nasal cavity.

Also provided is a method of enhancing sensory perception of a volatile oil in the oral cavity. The volatile oil is included in a confection designed to dissolve in the oral cavity. The confection also contains an amount of a volatile oil-modifying agent to modify the sensory perception of the volatile oil released in the oral cavity. The modifying agent is undetected as a separate agent but sensorially organoleptic sensations of the oils, such as bitterness, are substantially eliminated.

Unlike the prior art approaches to flavor modification, the use of capsicum in this invention to enhance the flavor delivery of essential oils is achieved without detection of the capsicum. Further, the prior art use of capsicum is largely limited to providing pungent flavor. Indeed, the flavor enhancing qualities of capsicum on essential oils has heretofore been unrealized. The prior art also does not disclose or suggest the ability of capsicum to reduce the bitterness of essential oils as they are released from compressed tablets into the oral cavity.

As a result of the present invention, an improved confectionery product can be provided which has enhanced flavor properties as well as substantial reductions in unpleasant organoleptic sensations such as bitterness upon the release of the volatile oil from the confection in the oral cavity.

For a better understanding of the present invention, together with other and further objects, reference is made to the following description and its scope will be pointed out in the appended claims.

DETAILED DESCRIPTION OF THE INVENTION

It has now been suprisingly found that the disadvantages associated with confections containing a volatile oil which imparts a bitter taste upon release in the oral cavity can be overcome by using the novel method and composition of the present invention. The novel confection contains a volatile oil and a modifying agent, preferably capsicum, present in an amount which is undetected as a separate ingredient in the oral cavity, but nevertheless has the ability to modify sensory perception of the volatile oil.

In a preferred embodiment, the confection contains both menthol and eucalyptus as the volatile oil component and the volatile oil modifying agent is capsicum oleoresin present in an amount of from about 1 to about 30 ppm. In this embodiment, the confection confers medicinal benefits by providing active ingredients which relieve irritations of the nasopharyngeal region caused by coughing as well as providing a decongestant effect in the nasal cavity by vapor action released from the confection.

In an alternative embodiment, there is also provided a confection which contains non-medicinal volatile oils which impart a flavor sensation in the oral cavity upon dissolving in the oral cavity. In this embodiment, the confection also contains a volatile oil-modifying agent which enhances the impact of the volatile oil released from the confection in the oral cavity. The volatile oil-modifying agent reduces the perceived bitterness, pungency, or other undesirable organoleptic sensation.

The preparation of confectionery formulations is historically well known and has changed little through the years. Confectionery items have been classified as either "hard" confectionery or "soft" confectionery. The volatile oil-modifying agent of the present invention can be incorporated by admixing the modifying agent into conventional hard and soft confections.

Hard confectionery may be processed and formulated by conventional means. In general, a hard confectionery has a base composed of a mixture of sugar and other carbohydrate bulking agents kept in an amorphous or glassy condition. This form is considered a solid syrup of sugars generally having from about 0.5% to about 1.5% moisture. Such materials normally contain up to about 92% corn syrup, up to about 55% sugar and from about 0.1% to about 5% water, by weight of the final composition. The syrup component is generally prepared from corn syrups high in fructose, but may include other materials. Further ingredients such as flavorings, sweeteners, acidulants, colorants and so forth may also be added.

Such confectionery may be routinely prepared by conventional methods such as those involving fire cookers, vacuum cookers, and scraped-surface cookers also referred to as high speed atmospheric cookers.

Fire cookers involve the traditional method of making a candy base. In this method, the desired quantity of carbohydrate bulking agent is dissolved in water by heating the agent in a kettle until the bulking agent dissolves. Additional bulking agent may then be added and cooking continued until a final temperature of 145° to 156° C. is achieved. The batch is then cooled and worked as a plastic-like mass to incorporate additives such as flavors, colorants and the like.

A high-speed atmospheric cooker uses a heat-exchanger surface which involves spreading a film of candy on a heat exchange surface, the candy is heated to 165° to 170° C. in a few minutes. The candy is then rapidly cooled to 100° to 120° C. and worked as a plastic-like mass enabling incorporation of the additives, such as flavors, colorants and the like.

In vacuum cookers, the carbohydrate bulking agent is boiled to 125° to 132° C., vacuum is applied and additional water is boiled off without extra heating. When cooking is complete, the mass is a semi-solid and has a plastic-like consistency. At this point, flavors, colorants, and other additives are admixed in the mass by routine mechanical mixing operations.

The optimum mixing required to uniformly mix the flavors, colorants and other additives during conventional manufacturing of hard confectionery is determined by the time needed to obtain a uniform distribution of the materials. Normally, mixing times of from 4 to 10 minutes have been found to be acceptable.

Once the candy mass has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, *Pharmaceutical Dosage Forms: Tablets,* Volume 1 (1980), Marcel Dekker, Inc., New York, N.Y. at pages 339 to 469, which disclosure is incorporated herein by reference.

The apparatus useful in accordance with the present invention comprises cooking and mixing apparatus well known in the confectionery manufacturing arts, and selection of the specific apparatus will be apparent to the artisan.

Similar to hard confectionery, soft confectionery may be utilized in this invention. The preparation of soft confections, such as nougat, involves conventional methods, such as the combination of two primary components, namely (1) a high boiling syrup such as corn syrup, hydrogenated starch hydrolysate or the like, and (2) a relatively light textured frappe, generally prepared from egg albumin, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring, additional carbohydrate bulking agent, colorants, preservatives, medicaments, mixtures thereof and the like may be added thereafter also under agitation. A general discussion of the composition and preparation of nougat confections may be found in B. W. Minifie, *Chocolate, Cocoa and Confectionery:* Science and Technology, 2nd edition, AVI Publishing Co., Inc., Westport, Conn. (1980), at pages 424–425, which disclosure is incorporated herein by reference.

The procedure for preparing the soft confectionery involves known procedures. In general, the frappe component is prepared first and thereafter the syrup component is slowing added under agitation at a temperature of at least about 65° C., and preferably at least about 100° C. The mixture of components is continued to be mixed to form a uniform mixture, after which the mixture is cooled to a temperature below 80.C, at which point, the flavor may be added. The mixture is further mixed for an additional period until it is ready to be removed and formed into suitable confectionery shapes.

The flavoring components of the confection are flavors having an associated bitter taste or other unpleasant after taste. These flavoring components may be chosen from natural and synthetic flavoring liquids such as volatile oils, synthetic flavor oils, flavoring aromatic and oils, liquids, oleoresins or extracts derived from plants, leaves, flowers, fruits, stems and combinations thereof. Non-limiting representative examples of volatile oils include spearmint oil, cinnamon oil, oil of wintergreen (methyl saliclate), peppermint oil, menthol, clove oil, bay oil, anise oil, eucalyptus oil, thyme oil, cedar leaf oil, oil of nutmeg, allspice oil, oil of sage, mace extract, oil of bitter almonds, and cassia oil. In addition, the confection may also contain artificial, natural or synthetic flavors including fruit flavors such as vanilla, and citrus oils including lemon, orange, grape, lime and grapefruit and fruit essences including apple, pear, peach, grape, strawberry, raspberry, cherry, plum, pineapple, apricot and so forth.

Other useful flavorings include aldehdydes and esters such as benzaldehyde (cherry, almond), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl adehyde (cherry, almond), 2,6-dimethyl-octanal (green fruit), and 2-dodecenal (citrus, mandarin), mixtures thereof and the like.

In the instance where sweeteners are utilized, the present invention contemplates the inclusion of those sweeteners well known in the art, including both natural and artificial sweeteners. The sweeteners may be chosen from the following non-limiting list: sugars such as sucrose, glucose (corn syrup), dextrose, invert sugar, fructose, and mixtures thereof, saccharin and its various salts such as the sodium or calcium salt; cyclamic acid and its various salts such as the sodium salt; the dipeptide sweeteners such as aspartame, dihydrochalcone compounds, glycyrrhizin; *Stevia Rebaudiana* (Stevioside); chloro derivatives of sucrose; dihydroflavinol; hydroxyguaiacol esters; L-amino dicarboxylic acid gem-diamines; L-aminodicarboxylic acid aminoalkenoic acid ester amides; and sugar alcohols such as sorbitol, sorbitol syrup, mannitol, xylitol, and the like. Also contemplated as an additional sweetener is the non-fermentable sugar substitute (hydrogenated starch hydrolysate) which is described in U.S. Reissue Pat. No. 26,959. Also contemplated is the synthetic sweetener 3,6-dihydro-6-methyl1-1-1,2,3-oxathiazin-4-one-2,2-dioxide, particularly the potassium (acesulfame-K), sodium and calcium salts thereof as described in German Patent No. 2,001,017.7.

In addition, the confection may also contain suitable auxiliary flavorings including both natural and artificial flavors, and mints such as peppermint, artificial vanilla, cinnamon, various fruit flavors, both individual and mixed. Such flavorings are generally utilized in amounts that will vary depending upon the particular confection and volatile oil selected.

The confection may also include a colorant. The colorants may be selected from any of the numerous dyes suitable for food, drug and cosmetic applications, and known as FD&C dyes and the like. The materials acceptable for the foregoing spectrum of use are preferably water-soluble. Illustrative examples include indigoid dye, known as FD&C Blue No. 2, which is the disodium salt of 5,5'-indigotindisulfonic acid. Similarly, the dye known as FD&C Green No. 1 comprises a triphenylmethane dye and is the monosodium salts of 4-[4-N-ethyl-p-sulfobenzylamino) diphenylmethylane]-[1-(N-ethyl-N-p-sulfoniumbenzyl)-2-5-cyclohexadieneimine]. A full recitation of all FD&C and D&C dyes and their corresponding chemical structures may be found in the Kirk-Othmer Encyclopedia of Chemical Technology, in Volume 5, pages 857–884, which is incorporated herein by reference.

In the case of a hard boiled cough drop-type confection, the volatile oil component is present in an amount from about 0.05 to about 1.0% by weight depending upon the confection, the volatile oil selected, and additional flavorings or sweeteners if added.

The volatile oil-modifying agent is preferably capsicum oleoresin. To effect the novel volatile oil enhancing properties of the present invention the modifying agent is present in an amount of from about 1 to about 150 ppm of the confection. The preferred range of capsicum is from about 5 to about 80 ppm, while the most preferred range is from about 9 to about 50 ppm of the confection.

The capsicum is available from *Capsicum minimum, Capsicum frutescens, Capsicum annuum,* and similar varieties. Commercially, the fruits of capsicum are referred to as chilies or as peppers. These fruits are known for their extreme potency of bite, pungency and characteristic odor.

Capsicum oleoresin is a dark red or orange-red liquid obtained by solvent extraction of a dried ripe fruit of *Capsicum frutescens* or *Capsicum annuum*. The capsicum oleoresin has a characteristic odor and extremely high bite. For example, usually within the range of 250,000 to 1,000,000 Scoville heat units. Capsicum oleoresin also has a distinct burning effect in the throat and posterior portion of the mouth.

Although capsicum and capsicum oleoresin are considered to be potent sources of peppery or pungent flavor, it has now been found that they enhance flavor delivery of volatile oils when present in amounts ranging from about 1 ppm to about 30 ppm. Key, however, to the present invention is the discovery that when capsicum is present in confections in the amounts set forth above, the capsicum is undetectable in the oral cavity yet at the same time provides enhanced flavor delivery of the companion volatile oil.

With respect to confectionery compressed tablet formulations, such will contain a tablet granulation base and various additives such as sweeteners and flavors. The tablet granulation base employed will vary depending upon factors such as the type of base used, friability desired and other components used to make the final product. The confectionery compressed tablet made in accordance with the present invention, however, contains a volatile oil and a volatile oil-modifying agent in amounts similar to the above cough drop example. These confections generally contain sugars in amounts up to 95% by weight of the composition. The confectionery compressed tablet may additionally include tablet excipients such as binders or lubricants, as well as flavoring agents and coloring agents.

The variations that one may practice with regard to these confections are wide ranging and within the ability of those skilled in the art particularly with regard to the use of additional composition fillers, flavoring adjuncts, the use of coloring agents, etc.

As previously mentioned, the volatile oil component of the confection may include menthol. In particular, the most important commercial source is l-menthol. Commercial l-menthol is isolated principally from the oil of *Mentha arvensis*. The process involves cooling of the oil and purifying the crystals formed. Menthol possess a distinct peppermint flavor and gives the impression of cooling the mouth and skin.

L-menthol and eucalyptus oil may be combined to provide the volatile oil component of the confection. When so combined, the menthol-eucalyptus is useful as an adjunct to coughing cold therapy. Eucalyptus is believed to impart decongestant type activity while menthol provides soothing of the mouth and throat areas. When the volatile oil modifying agent capsicum is combined with the above volatile oil combination menthol-eucalyptus, it has been found that the modifying agent substantially ameliorates the unpleasant organoleptic experience often detected when confectionery formulations containing the above ingredients dissolve in the oral cavity.

Tests were conducted by using the confection of the present invention to compare it with confection products not containing a volatile oil-modifying agent, and it was found that not only were the flavor enhancing properties of the capsicum evident but also that such inventive confections were undetectable for peppery taste.

EXAMPLES

The following examples serve to provide further appreciation of the invention but are not meant in any way to restrict the effective scope of the invention.

EXAMPLE 1

A control hard boiled cough drop was prepared using the following formulation.

| | CONTROL SAMPLES | |
|---|---|---|
| | PERCENT BY WEIGHT | |
| INGREDIENT | A | B |
| Sugar (fine granulated) | 54.7830 | 54.8185 |
| Corn syrup 43 Baume | 44.8210 | 44.8515 |
| Citric acid | 0.2160 | — |
| l-menthol | 0.1000 | 0.1733 |
| Eucalyptus oil | 0.0800 | 0.1567 |
| Capsicum Oleoresin | — | — |
| | 100.000 | 100.000 |

Additionally, the inventive confections with the volatile oil modifying agent capsicum oleoresin were prepared in accordance with the following formula.

| | INVENTIVE SAMPLES | |
|---|---|---|
| | PERCENT BY WEIGHT | |
| INGREDIENT | SAMPLE C | SAMPLE D |
| Sugar-fine granulated | 54.7820 | 54.8190 |
| Corn syrup 43 Baume | 44.8210 | 44.8510 |
| Citric acid | 0.2160 | — |
| l-menthol | 0.1000 | 0.1711 |
| Eucalyptus oil | 0.0800 | 0.1546 |
| Capsicum Oleoresin | 0.0010 | 0.0043 |
| | 00.0000 | 100.0000 |

Each of the above were then subject to testing for sensory evaluation. The results are set forth below.

| EXPERT PANEL TESTING | | |
|---|---|---|
| SPECIMEN | FLAVOR | BITTERNESS |
| Control A | Moderate | Detectable |
| Control B | Strong | Quite Noticable |
| Sample C | Excellent | Slightly Perceivable |
| Sample D | Excellent | Slightly Perceivable |

Control Samples A and B were described as having a harsh flavor with a strong menthol presence and associated bitterness. Inventive Sample C and D, on the other hand, were described as having significantly less bitterness and an organoleptically pleasing menthol-eucalyptus flavor with more enhanced menthol cooling than the Controls.

As can be seen, the confection products of the present invention provided favorable results when compared to the control samples. Whereas in the past, confections containing menthol and/or eucalyptus often provided undesired organoleptic sensations such as bitterness, the inventive compositions clearly demonstrate decreased bitterness upon the release of the essential oil(s) into the oral cavity. In addition, organoleptic sensations in the oral cavity are enhanced with the product of the present invention.

Thus, while there has been described what are presently believed to be the preferred embodiment of the present invention, and further embodiments will be realized by those skilled in the art, and it is intended to claim all such embodiments as come within the true scope of the invention.

What is claimed is:

1. A confection for dissolving in the oral cavity comprising:
   (a) a volatile oil; and
   (b) a volatile oil-modifying agent in an amount which is sensorially undetected in the oral cavity but sufficient to modify sensory perception of said volatile oil as it is released in the oral cavity.

2. The confection of claim 1 wherein said capsicum oleoresin is present in an amount of from about 5 to about 80 ppm in said confection.

3. The confection of claim 2 wherein said capsicum oleoresin is present in an amount of from about 9 to about 50 ppm in said confection tablet.

4. The confection of claim 1 wherein said volatile oils are selected from the group consisting of menthol, l-menthol, anise, caraway, cinnamon, clove, coriander, eucalyptus, fennel, lavender, lemon, orange, orange flower, peppermint, pine needle, spearmint, and mixtures thereof.

5. The confection of claim 1 wherein said volatile oil is present in an amount of from about 0.05 to about 1.0 percent by weight of said confection.

6. The confection of claim 5 wherein said volatile oil is present in an amount of from about 0.06 to about 0.75 percent by weight of said confection.

7. The confection of claim 6 wherein said volatile oil is present in an amount of from about 0.15 to about 0.50 percent by weight of said confection.

8. A method of enhancing sensory perception of volatile oils in the oral cavity comprising:
   providing a volatile oil-modifying agent in an amount which is sensorially undetected in the oral cavity but sufficient to modify the sensory perception of said volatile oil as it is released in the oral cavity.

9. The method of claim 8 wherein said volatile oils are selected from the group consisting of menthol, l-menthol, anise, caraway, cinnamon, clove, coriander, eucalyptus, fennel, lavender, lemon, orange, orange flower, peppermint, pine needle, spearmint, and mixtures thereof.

10. A medicinal tablet for dissolving in the oral cavity comprising:
    (a) menthol; and
    (b) a menthol modifying agent in an amount which is sensorially undetected in the oral cavity but sufficient to modify sensory perception of said menthol as it is released from said medicinal tablet in the oral cavity.

* * * * *